United States Patent
Ferrari et al.

(10) Patent No.: US 9,125,925 B2
(45) Date of Patent: Sep. 8, 2015

(54) ABNORMAL INTRAOCULAR PRESSURE TREATMENT

(71) Applicants: Horphag Research (Luxembourg) Holdings SA, Luxembourg (LU); Indena S.P.A., Milan (IT)

(72) Inventors: Victor Ferrari, Cointrin (CH); Salvatore Malandrino, Milan (IT); Carolina Burki, Cointrin (CH); Frank Schoenlau, Munster (DE)

(73) Assignees: Horphag Research IP (MIR) Ltd., Limassol (CY); Indena S.P.A., Milan (IT)

( * ) Notice: Subject to any disclaimer, the term of this patent is extended or adjusted under 35 U.S.C. 154(b) by 0 days.

(21) Appl. No.: 13/886,565

(22) Filed: May 3, 2013

(65) Prior Publication Data

US 2013/0244961 A1 Sep. 19, 2013

Related U.S. Application Data

(62) Division of application No. 12/863,073, filed as application No. PCT/EP2009/000255 on Jan. 16, 2009, now abandoned.

(60) Provisional application No. 61/011,561, filed on Jan. 18, 2008.

(51) Int. Cl.
*A61K 31/353* (2006.01)
*A61K 31/7048* (2006.01)
*A61K 36/15* (2006.01)
*A61K 36/45* (2006.01)

(52) U.S. Cl.
CPC ............ *A61K 31/7048* (2013.01); *A61K 31/353* (2013.01); *A61K 36/15* (2013.01); *A61K 36/45* (2013.01)

(58) Field of Classification Search
CPC .................................................... A61K 31/353
USPC ............................................................ 514/27
See application file for complete search history.

(56) References Cited

U.S. PATENT DOCUMENTS

| 6,573,299 B1 | 6/2003 | Petrus |
| 2002/0164388 A1 | 11/2002 | Sosnowski et al. |
| 2008/0181972 A1 | 7/2008 | Amico et al. |

FOREIGN PATENT DOCUMENTS

| WO | 02 20028 A2 | 3/2002 |
| WO | 03 084559 A1 | 10/2003 |

OTHER PUBLICATIONS

Rohdewald, P., "A Review of the French Maritime Pine Bark Extract (Pycnogenol), A Herbal Medication with a Diverse Clinical Pharmacology", International Journal of Clinical Pharmacology and Therapeutics, vol. 40, No. 4, Apr. 1, 2002, pp. 158-168.
Steigerwalt et al., "Effects of Mirtogenol on ocular blood flow and intraocular hypertension in asymptomatic subjects", Molecular Vision, vol. 14, Jul. 2008, pp. 1288-1292.
International Search Report for PCT/EP2009/000255, dated Apr. 1, 2009.
Written Opinion for PCT/EP2009/000255, dated Apr. 1, 2009.

*Primary Examiner* — Zohreh Fay
(74) *Attorney, Agent, or Firm* — Hoffmann & Baron, LLP

(57) ABSTRACT

Methods and compositions for reducing intraocular pressure in a patient, particularly a human patient, are described. In particular, compositions are disclosed that contain an anthocyanoside or an extract comprising it, a proanthhocyanidin or an extract comprising it and combinations thereof. The compositions are useful for lowering intraocular pressure.

4 Claims, No Drawings

ABNORMAL INTRAOCULAR PRESSURE TREATMENT

CROSS-REFERENCE TO RELATED APPLICATIONS

This application is a divisional application of U.S. patent application Ser. No. 12/863,073 filed Oct. 1, 2010, which application is the National Stage of International Application No. PCT/EP2009/000255 filed Jan. 16, 2009, which claims the benefit of U.S. Provisional Patent Application No. 61/011,561, filed Jan. 18, 2008, the contents of which are incorporated by reference herein.

FIELD OF THE INVENTION

This invention relates to methods and compositions for treating or reducing high or abnormal intraocular pressure.

Intraocular pressure is the pressure, generally measured in millimeters of mercury (mm Hg), of the fluid in the eye. Intraocular pressure is measured with an instrument called a tonometer. The most accurate of which is generally considered to be the applanation tonometer, which measures the force required to flatten a small area of central cornea after the eyes have been numbed.

Normal intraocular pressure is generally considered to range from 10 mm Hg to 21 mm Hg, with the average being about 16 mm Hg__ According to the National Eye Institute of the U.S. National Institutes of Health, elevated intraocular pressure affects between three and six million people in the United States. Elevated intraocular pressure is thought to be the leading risk factor for glaucoma which affects approximately two million people in the United States. Glaucoma is the leading cause of blindness in the United States and other industrialized countries.

Ocular hypertension occurs when a person has elevated intraocular pressure which has not affected vision or damaged the structure of the eye. Because approximately 1.5 million people in the United States were being treated with costly ocular hypotensive medications that carry the potential for serious and even life-threatening side effects, the National Eye Institute funded a study to determine whether lowering intraocular pressure in ocular hypertensive patients prevents or delays the onset of glaucoma. This study, the Ocular Hypertension Treatment Study (OHTS), was a five year randomized, controlled multicenter clinical trial. The study concluded that lowering intraocular pressure using commercially available topical antiglaucoma agents lowered the risk of developing glaucoma in five years from 9.5% to 4.4%.

Accordingly, there is a need for compositions, particularly natural compositions which can achieve their therapeutic effect with few or no side effects, that can be used to reduce high or abnormal intraocular pressure.

SUMMARY OF THE INVENTION

One aspect of the present invention provides methods for reducing intraocular pressure in a patient comprising administering to the patient a therapeutically effective amount of at least one of an anthocyanoside, a proanthocyanidin or a combination thereof (e.g., therapeutically effective amounts of at least one anthocyanoside and at least one proanthocyanidin) until intraocular pressure is reduced. According to some embodiments, the at least one anthocyanoside and/or at least one proanthocyanidin is one or more extracts comprising one or more anthocyanosides and/or one or more proanthocyanidins, respectively.

In another aspect, the present invention provides pharmaceutical compositions for the treatment or prevention of high or abnormal intraocular pressure comprising (1) a therapeutically effective amount of at least one of an anthocyanoside, a proanthocyanidin or a combination thereof (e.g., therapeutically effective amounts of at least one anthocyanoside and at least one proanthocyanidin), and (2) a pharmaceutically acceptable excipient. According to some embodiments, the at least one anthocyanoside and/or at least one proanthocyanidin is one or more extracts comprising one or more anthocyanosides and/or one or more proanthocyanidins, respectively.

DETAILED DESCRIPTION

Proanthocyanidins designate a group of flavonoids that includes the subgroups procyanidins, prodelphinidins and propelargonidins. Proanthocyanidins are homogeneous or heterogeneous polymers consisting of the monomer units catechin or epicatechin, which are connected either by 4-8 or 4-6 linkages, to the effect that a great number of isomer proanthocyanidins exist. Typically, the proanthocyanidins oligomers have a chain length of 2-12 monomer units. Proanthocyanidins may be synthesized or extracted from a plant material. Proanthocyanidins are extracted from plant material by conventional methods using solvents like water, ethanol or acetone or fluid carbon dioxide. The extracts are purified by solvent/solvent extraction, ultra filtration or chromatographic procedures. The purified extracts are concentrated by solvent evaporation, freeze drying or spray drying. Nonlimiting examples of plant material sources of proanthocyanidins include grape seeds, grape skin, pine barks, ginkgo leaves, peanuts, cocoa beans, tamarind, tomato, almond, apple, cranberry, blueberry, and tea leaves.

A well-known product containing proanthocyanidins, which is available in trade as a preparation of a food supplement under the name Pycnogenol®, is an extract of the maritime pine bark (*Pinus pinaster*). Pycnogenol®, the extract from French maritime pine bark (*Pinus pinaster*), is a registered trademark belonging to Horphag Research, Ltd. Pycnogenol® is a standardized bark extract of the French maritime pine *Pinus pinaster*, Aiton, subspecies Adantica des Villar (Pycnogenol®, Horphag Research Ltd., UK). The quality of this extract is specified in the United States Pharmacopeia (USP 28) (Maritime Pine Extract. In: United States Pharmacopeia. Rockville: United States Pharmacopeial Convention, Inc.; 2005. pp. 2115-2116.). Between 65-75% of Pycnogenol® are procyanidins comprised of catechin and epicatechin subunits with varying chain lengths (Rohdewald P. A review of the French maritime pine bark extract (Pycnogenol), an herbal medication with a diverse clinical pharmacology (Int J Clin Pharmacol Ther 2002; 40: 158-168.). Other constituents are polyphenolic monomers, phenolic or cinnamic acids and their glycosides (Id.).

*Pinus pinaster* (*P. pinaster*) and *Pinus maritima* (*P. maritime*), are understood to refer to the same organism. Hence, these terms, as used herein, are interchangeable.

Another group of naturally occurring flavonoids is the anthocyanins or anthocyanosides. Anthocyanins are colored substances that are responsible for the red, purple and blue colors of many fruits and flowers. They are prevalent in and responsible for the colors of fruits that include blueberries, bilberries, blackberries, cherries, plums, currant, chokeberries, grapes, strawberries, raspberries, boysenberries, marionberries, cranberries and elderberries. Anthocyanins may be synthesized or extracted from a plant material. Anthocyanins are extracted from plant material by conventional methods using solvents like water, ethanol or acetone or fluid carbon dioxide. The extracts are purified by solvent/solvent extraction, ultra filtration or chromatographic procedures.

A well-known product containing anthocyanins, which is available in trade as a preparation of a food supplement under the name Mirtoselect®, is an extract of bilberry fruit (*Vaccinium myrtillus* L.). Mirtoselect®, the extract from fresh bilberry fruits (*Vaccinium myrtillus* L.), is a registered trademark belonging to Indena S.p.A. Mirtoselect® is a standardized fruit extract of the bilberry *Vaccinium myrtillus* L. (Mirtoselect®, Indena S.p.A., Milan, Italy). This extract contains anthocyanins and is characterized by a specific and reproducible HPLC profile.

The terms "anthocyanins" and "anthocyanosides" are understood to refer to the same compounds. Hence, these terms, as used herein, are interchangeable.

By an "effective" amount or a "therapeutically effective amount" of a drug or pharmacologically active agent is meant a nontoxic but sufficient amount of the drug or agent to provide the desired effect, i.e., reduction of intraocular pressure.

An appropriate "effective" amount in any individual case may be determined by one of ordinary skill in the art using routine experimentation.

The term "extract", as used herein includes any preparation obtained from plants, fruits or vegetables using an extraction method.

According to one aspect of the present invention, methods are provided for reducing intraocular pressure in a patient, preferably a human patient, comprising administering to the patient a therapeutically effective amount of at least one of an anthocyanoside, a proanthocyanidin or a combination thereof (e.g., therapeutically effective amounts of at least one anthocyanoside and at least one proanthocyanidin) until intraocular pressure is reduced. According to certain preferred embodiments, the at least one anthocyanoside and/or at least one proanthocyanidin is one or more extracts comprising one or more anthocyanosides and/or one or more proanthocyanidins, respectively.

According to some embodiments, the patient has an intraocular pressure, in at least one eye, of between 15 mm Hg to 18 mm Hg, between 18 mm Hg to 21 mm Hg, between 21 mm Hg to 25 mm Hg, or between 25 mm Hg to 30 mm Hg. According to some embodiments, the patient has an intraocular pressure, in at least one eye, of greater than 15 mm Hg, greater than 21 mm Hg, greater than 25 mm Hg, or greater than 30 mm Hg.

In some embodiments, the one or more extracts comprising one or more proanthocyanidins is a plant extract. In preferred embodiments, the plant extract is a pine bark extract, a grape seed extract or an extract of apples, peanut skin, walnuts, pomegranates, tomatoes, almonds, tea, hawthorn or cocoa. In more preferred embodiments, the pine bark extract is from a pine of the *Pinus pinaster* species. In yet other preferred embodiments, the grape seed extract is from *Vitis vinifera* species.

According to some embodiments, the one or more extracts comprising one or more anthocyanosides is a plant extract. In preferred embodiments, the plant extract is a red fruit extract. In some embodiments, the red fruit extract is from blueberry, cherry, cranberry, red grapes, black cherry, blackcurrant, chokeberry, eggplant, orange, raspberry, or redcurrant. In more preferred embodiments, the red fruit extract is from *Vaccinium myrtillus*.

In some embodiments of these methods, the therapeutically effective amounts of the at least one anthocyanoside and at least one proanthocyanidin administered is between 0.5 and 10 mg/kg/day.

In certain preferred embodiments, the patient has ocular hypertension. In particularly preferred embodiments, the ocular hypertension comprises the following symptoms: (a) an intraocular pressure greater than 21 mm Hg in one or both eyes as measured by applanation tonometry on 2 or more occasions; (b) an absence of glaucomatous defects on visual field testing; (c) normal appearance of the optic disc and nerve fiber layer; and (d) open angles on gonioscopy, with no history of angle closure.

According to another aspect of the present invention, pharmaceutical compositions are provided for the treatment or prevention of high or abnormal intraocular pressure, comprising (1) a therapeutically effective amount of at least one of an anthocyanoside, a proanthocyanidin or a combination thereof (e.g., therapeutically effective amounts of at least one anthocyanoside and at least one proanthocyanidin), and (2) a pharmaceutically acceptable excipient. According to certain preferred embodiment, the at least one anthocyanoside and/or at least one proanthocyanidin is one or more extracts comprising one or more anthocyanosides and/or one or more proanthocyanidins, respectively.

In some embodiments, the one or more extracts comprising one or more proanthocyanidins is a plant extract. In preferred embodiments, the plant extract is a pine bark extract, a grape seed extract or an extract of apples, peanut skin, walnuts, pomegranates, tomatoes, almonds, tea, hawthorn or cocoa. In more preferred embodiments, the pine bark extract is from a pine of the *Pinus pinaster* species. In yet other preferred embodiments, the grape seed extract is from *Vitis vinifera* species.

In some embodiments, the one or more extracts comprising one or more anthocyanosides is a plant extract. In preferred embodiments, the plant extract is a red fruit extract. In some embodiments, the red fruit extract is from blueberry, cherry, cranberry, red grapes, black cherry, blackcurrant, chokeberry, eggplant, orange, raspberry, or redcurrant. In more preferred embodiments, the red fruit extract is from *Vaccinium myrtillus*.

In some embodiments, the compositions are administered at a dosage of 50 to 500 mg/day of at least one proanthocyanidin or an extract comprising it and 100 to 1000 mg/day of at least one anthocyanoside or an extract comprising it.

According to some embodiments, these compositions are for the treatment of ocular hypertension. In preferred embodiments, the ocular hypertension comprises the following symptoms: (a) an intraocular pressure greater than 21 mm Hg in one or both eyes as measured by applanation tonometry on 2 or more occasions; (b) an absence of glaucomatous defects on visual field testing; (c) normal appearance of the optic disc and nerve fiber layer; and (d) open angles on gonioscopy, with no history of angle closure.

It will be appreciated by those skilled in the art that various omissions, additions and modifications may be made to the invention described above without departing from the scope of the invention, and all such modifications and changes are intended to fall within the scope of the invention, as defined by the appended claims. All references, patents, patent applications or other documents cited are herein incorporated by reference in their entirety.

EXAMPLE 1

Effects of Pycnogenol® and Mirtoselect® on Ocular Measurements

A total of twenty patients (12 males, 8 females) were used as the study group. These patients had an average age of 45.8

(standard deviation of 6.5). In addition, 18 patients (9 males, 9 females) with an average age of 44.7 (standard deviation of 9.2) were used as untreated controls. 18 patients (9 males and 9 females) with an average age of 46.3 (standard deviation of 7_3) were used as the Pycnogenol® group; an additional 18 patients (9 males and 9 females) with an average age of 47.6 (standard deviation of 8.4) were used as the Mirtoselect® group.

The patients were characterized with the following characteristics: (1) the patient had moderately high-intraocular pressure; (2) the patient had a cup to disc ratio of more than 0.5; (3) central corneal thickness of less than 555 microns; (4) the patient had minimal or no field of vision defects; and (5) the patient was not on medication.

Treatment:

Each patient of the study group was treated for a period of three to six months with a composition comprising 80 mg of Pycnogenol® (pine bark extract) and 160 mg of Mirtoselect® (bilberry extract) per day. The composition was administered in two doses (each 40 mg of Pycnogenol® and 80 mg of Mirtoselect®) taken morning and night orally. The control group was untreated while the Pycnogenol® and Mirtoselect® groups received the same amount as present in the composition of the study group (Pycnogenol® 40+40 mg; Mirtoselect® 80+80 mg). The reduction of intraocular pressure was considered positive if intraocular pressure was reduced by more than 2.5 mm Hg.

TABLE 1

Pressure Measurement

| Treatment | At baseline | 3 months | | |
|---|---|---|---|---|
| | | Decrease in ocular pressure* | Increase in ocular pressure | Visual acuity |
| Study Group (Pycnogenol® and | 25.2; SD 3.1 mmHg | 19/20** | 0/20 | No change |
| Pycnogenol® Group | 24.9; SD 2.9 mmHg | 4/18* | 0/18 | No change |
| Mirtoselect® Group | 25.1; SD 3.0 mmHg | 5/18* | 1/18 | No change |
| Untreated Group (Control) | 24.6; SD 2_8 mmHg | 0/18 | 2/18 | No change |

*Number of patients with a reduction of intraocular pressure of more than 2.5 mmHg.
**Indicates significant change both from initial value and in comparison with control, Pycnogenol and Mirtoselect groups.

Comparison of Patients Treated With Pycnogenol® and Mirtoselect® to Patients Treated With Pycnogenol® Alone or Mirtoselect® Alone Significantly, we found that the improvements in ocular symptoms were improved in patients treated with Pycnogenol® and Mirtoselect® compared to patients treated with either Pycnogenol® or Mirtoselect® alone. The effect of a combination of Pycnogenol® and Mirtoselect® cannot be accounted for merely by the additive effects of pine bark and bilberry extracts alone since the observed effect is higher than that would be expected if the ingredients were used individually. That is, the reduction in intraocular pressure by using Pycnogenol® and Mirtoselect® cannot be achieved by the use of Pycnogenol® alone or by the use of Mirtoselect® alone—regardless of dosage. Because of this, a statistically significant synergistic effect is achieved when the two ingredients are administered together particularly when administered in the ratios disclosed in this experiment.

What is claimed:

1. A pharmaceutical composition for the treatment of high or abnormal intraocular pressure comprising (1) about 160 milligrams of at least one *Vaccinium myrtillus* extract per day, (2) about 80 milligrams of at least one pine bark extract per day, and (3) a pharmaceutically acceptable excipient.

2. The composition of claim 1, wherein said pine bark extract is from a pine of the *Pinus pinaster* species.

3. The composition of claim 1, for the treatment of ocular hypertension wherein said ocular hypertension comprises the following symptoms:

(a) an intraocular pressure greater than 21 mm Hg in one or both eyes as measured by applanation tonometry on 2 or more occasions;

(b) an absence of glaucomatous defects on visual field testing;

(c) normal appearance of the optic disc and nerve fiber layer; and (d) open angles on gonioscopy, with no history of angle closure.

4. The composition of claim 1, wherein said composition is orally administered.

* * * * *